(12) United States Patent
Yoo et al.

(10) Patent No.: US 6,289,184 B1
(45) Date of Patent: Sep. 11, 2001

(54) APPARATUS FOR MEASURING CONCENTRATION OF DEVELOPER OF LIQUID PRINTER

(75) Inventors: Yong-baek Yoo, Suwon; Kyu-cheol Shin, Kwacheon; Hee-guk Kwak, Suwon, all of (KR)

(73) Assignee: Samsung Electronics Co., Ltd., Kyungki-Do (KR)

( * ) Notice: Subject to any disclaimer, the term of this patent is extended or adjusted under 35 U.S.C. 154(b) by 0 days.

(21) Appl. No.: 09/576,202

(22) Filed: May 23, 2000

(30) Foreign Application Priority Data

May 31, 1999 (KR) .................................................. 99-19769

(51) Int. Cl.⁷ .................................................. G03G 15/10
(52) U.S. Cl. .............................. 399/57; 118/689; 399/64
(58) Field of Search .................................. 399/57, 58, 61, 399/62, 64, 30; 324/71.1; 118/689, 691

(56) References Cited

U.S. PATENT DOCUMENTS

| | | | |
|---|---|---|---|
| 4,204,766 | * | 5/1980 | Harada ................................. 399/57 X |
| 5,933,685 | * | 8/1999 | Yoo ........................................ 399/57 |
| 6,091,914 | * | 7/2000 | Yoo ........................................ 399/57 |

FOREIGN PATENT DOCUMENTS 04-251274 * 9/1992 (JP) .
05-332926 * 12/1993 (JP) .

* cited by examiner

Primary Examiner—Sophia S Chen
(74) Attorney, Agent, or Firm—Sughrue, Mion, Zinn, Macpeak & Seas, PLLC

(57) ABSTRACT

An apparatus for measuring the concentration of developer in a liquid printer, the apparatus includes a housing, a developer film forming device installed in the housing for forming a developer film, and a sensing device including a light source unit for emitting colored light corresponding to a range of wavelengths for which the light transmissivity is relatively low to a developer film of a selected color developer, and a photodetector installed corresponding to the light source unit and receiving the light emitted by the light source unit and transmitted through the developer film. Thus, a thin developer film is formed and the concentration of developer is measured by emitting light in a range of wavelengths for which the selected color developer has a relatively low light transmissivity to the developer film. The affect by the toner mixed with other color is relatively less and the concentration of developer can be measured close to the actual concentration although the developer is contaminated.

15 Claims, 6 Drawing Sheets

APPARATUS FOR MEASURING CONCENTRATION OF DEVELOPER OF LIQUID PRINTER

BACKGROUND OF THE INVENTION

1. Field of the Invention

The present invention relates to an apparatus for measuring the concentration of developer used in a liquid printer, and more particularly, to an apparatus for measuring the concentration of developer used in a liquid printer developer by forming a developer film and measuring the amount of light transmitted through the developer film.

2. Description of the Related Art

In general, a liquid electrophotographic printer is a device for forming an electrostatic latent image by selectively scanning a laser beam onto a photoreceptor medium such as a photoreceptor web or a photoreceptor drum and developing a toner image from the electrostatic latent image with developer which is a mixture of toner and a liquid carrier in a predetermined ratio.

A color liquid electrophotographic printer, as shown in FIG. 1, includes a plurality of development units 20 for developing an electrostatic latent image formed on the image recording surface of a photoreceptor web 1 which is one of photoreceptor media by a laser beam selectively scanned by a laser scanning unit (LSU) 10.

As shown in the drawing, the development units 20 are typically arranged to form a toner image in order of yellow (Y), magenta (M), cyan (C) and black (K) colors. Each development unit includes a container 21 for developer corresponding to the respective yellow (Y), magenta (M), cyan (C) and black (K) colors, and a developing portion 25 for receiving developer supplied from the container 21 by a developer supply apparatus 23 and for developing a toner image from the electrostatic latent image formed on the photoreceptor web 1.

The toner image developed at the developing portion 25 is dried at a drying unit 30 and transferred to a transfer roller 41. The transferred image is printed on a sheet of paper 45 supplied between the transfer roller 41 and the fusing roller 43. Any remaining developer after the development is collected in the container 21 through the developing portion 25.

Also, the liquid electrophotographic printer generally includes a concentration measuring apparatus 50 for measuring whether the concentration of the developer is appropriate. The concentration measuring apparatus 50 measures the concentration of developer by emitting light to the developer supplied to the developing portion 25 and measuring the light transmittance thereof.

However, as the toner image may not be completely transferred onto the transfer roller 41 during the transfer process, some toner may remain on the photoreceptor web 1. As the photoreceptor web 1 rotates, any remaining color toner is carrier along through the developing portions 25. In doing so, the remaining color toner may enter inside the developing portion 25 for developing a color different from the remaining color and be collected to the container 21 so as to contaminate the original developer color contained in the container 21. Also, even before the toner image reaches the drying unit 30, some of the developer adhering to the photoreceptor web 1 at the developing portion 25 enters the subsequent developing portions to contaminate the developers there.

When the developer is contaminated, the concentration measuring apparatus 50 detects a different concentration value from the actual concentration value due to the difference in the light transmittance of the different color toners. For example, in the case of yellow developer contaminated by a small amount of black developer, the concentration value detected by the concentration measuring apparatus 50 is greater than the actual value as the black contaminant causes the light transmittance of the yellow developer to sharply decrease. This is because the light color developers such as yellow, magenta and cyan have light transmittances of about 70–80% or more except for a particular wavelength range corresponding to the color of the developer, whereas black developer exhibits very low light transmittance with respect to light of most wavelengths.

Thus, when developer is contaminated by a different color, in particular, black toner, the concentration measuring apparatus 50 measures an incorrect concentration which is different from the actual concentration value. Also, if the sample of developer to be measured is thick and the developer is contaminated by black toner, the light transmittance approaches zero so that the concentration measurement cannot be performed.

SUMMARY OF THE INVENTION

To solve the above problems, it is an objective of the present invention to provide an apparatus which is less affected by mixed toner of other colors and measures the concentration of developer used in a liquid printer close to an actual concentration of developer although the developer is contaminated.

Accordingly, to achieve the above objective, there is provided an apparatus for measuring the concentration of developer in a liquid printer includes a housing, a developer film forming device installed in the housing for forming a developer film, and a sensing device including a light source unit for emitting colored light corresponding to a range of wavelengths for which the light transmissivity is relatively low to a developer film of a selected color developer, and a photodetector installed corresponding to the light source unit and receiving the light emitted by the light source unit and transmitted through the developer film.

Here, it is preferred in the present invention that the selected color developer is yellow, magenta or cyan color developers, and the color light is blue, green and red light in respect to yellow, magenta and cyan developer, respectively.

Also, it is preferred in the present invention that the blue, green and red light have wavelength ranges of about 400–470 nm, 500–580 nm and 630–700 nm, respectively, and that the blue, green and red light have wavelength ranges of about 436 nm, 546 nm and 700 nm, respectively.

Also, it is preferred in the present invention that the light source unit is a light emitting diode emitting blue, green or red light.

Also, it is preferred in the present invention that the light source unit comprises a white light source and a filter for passing blue, green or red light of the light emitted from the white light source.

Also, it is preferred in the present invention that the light source unit comprises a white light source, a spectrum member for splitting the light emitted from the white light source according to the wavelengths of the light, and an optical cable through which light spilt by the spectrum member is guided to the developer film, wherein the light is of a predetermined wavelength for which the light transmissivity of a selected color developer is relatively low.

Also, it is preferred in the present invention that the developer film forming device comprises a roller rotatably installed in the housing, a driving source for driving the roller to rotate, and a developer supply device for supplying developer to the roller so that a developer film can be formed according to the rotation of the roller.

Also, it is preferred in the present invention that a reflection member is provided on at least a part of the surface of the roller, and the light source unit and the photodetector are installed outside the roller to correspond to each other.

Also, it is preferred in the present invention that at least a part of the roller is formed of a transparent member, and the light source unit and the photodetector are installed inside and outside the roller, respectively, or vice versa such that they are facing each other through the transparent member.

BRIEF DESCRIPTION OF THE DRAWINGS

The above objective and advantages of the present invention will become more apparent by describing in detail a preferred embodiment thereof with reference to the attached drawings in which.

DETAILED DESCRIPTION OF THE INVENTION

Figure 2:
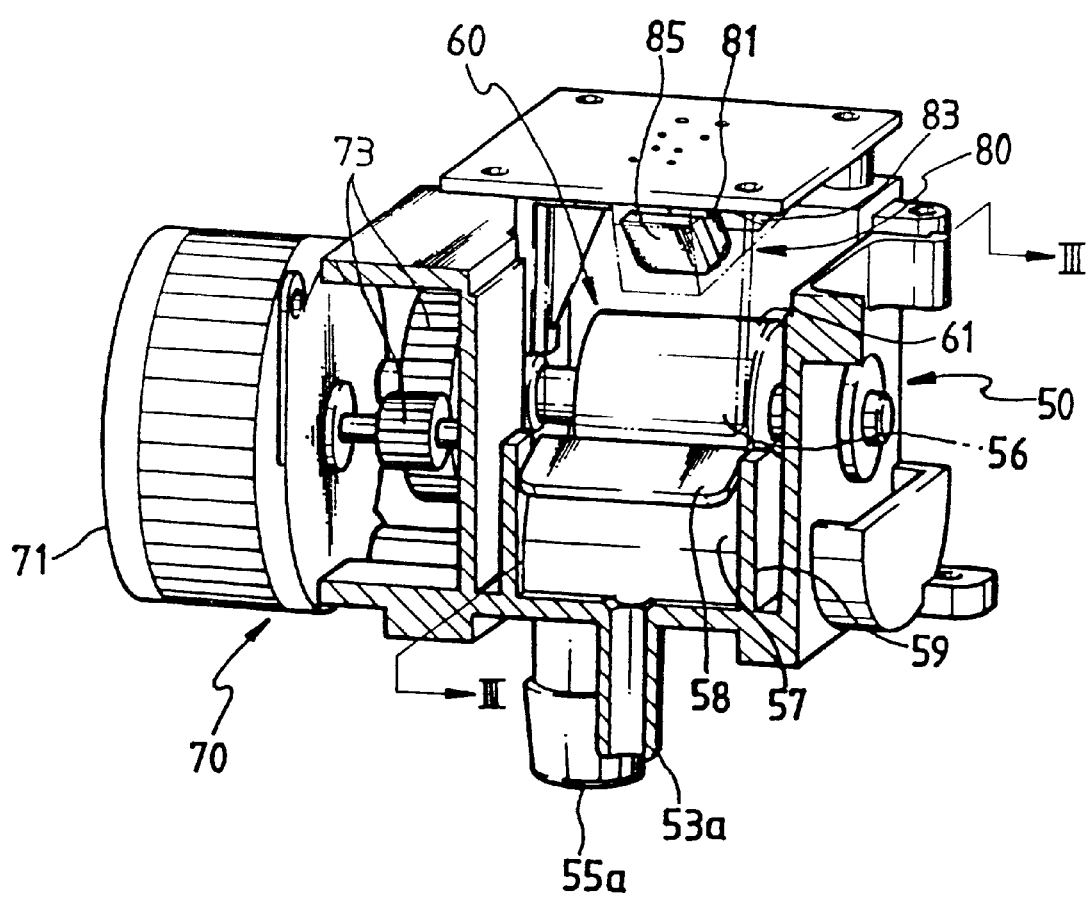
FIG. 2 is a partially cut-away perspective view showing an apparatus for measuring the concentration of developer of a liquid printer according to a preferred embodiment of the present invention.
Figure 3:
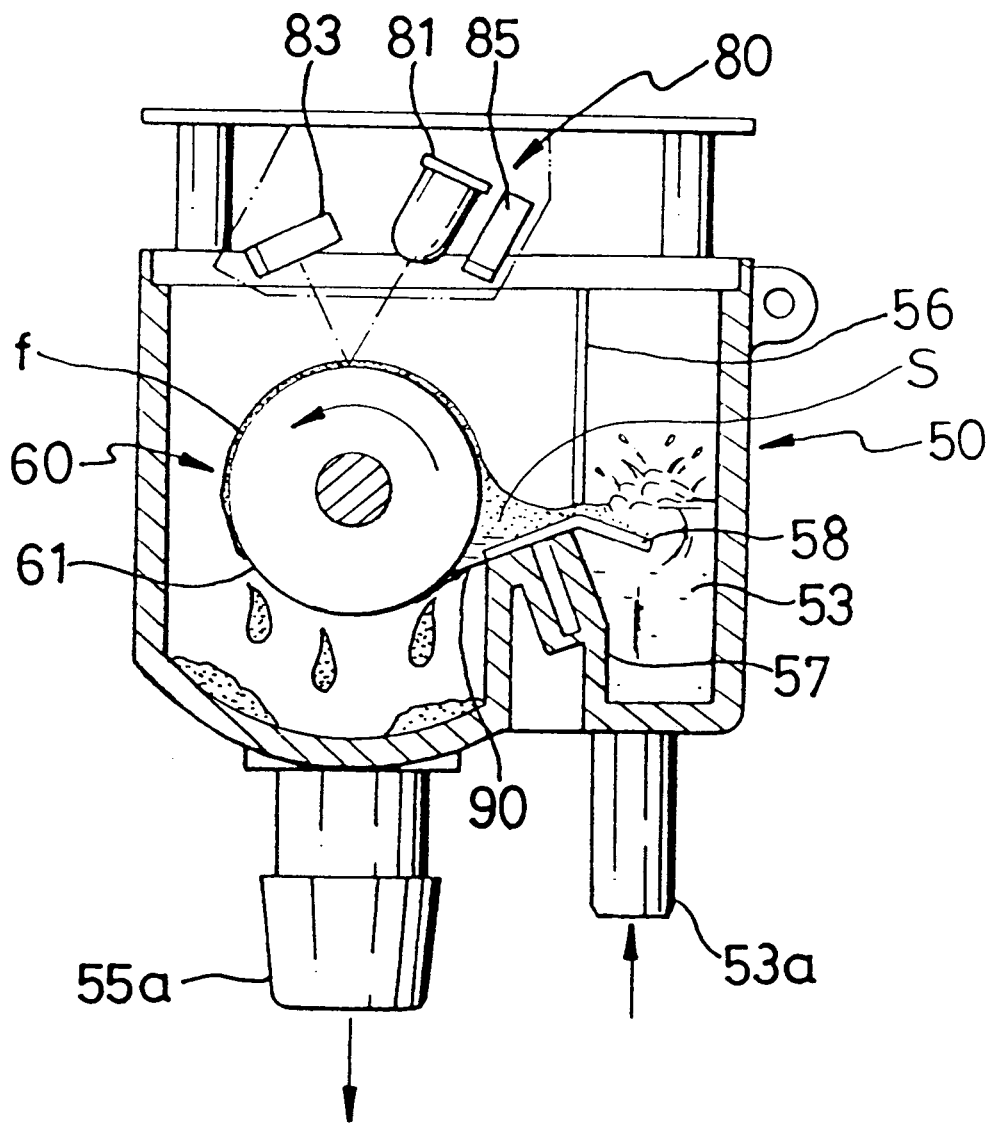
FIG. 3 is a sectional view taken along the line III—III.

Referring to FIGS. 2 and 3, an apparatus for measuring the concentration of developer according to a preferred embodiment of the present invention includes a housing 50, a device installed at the housing 50 for forming a developer film, and a sensing device 80 for detecting the concentration of a selected color developer by measuring the light transmissivity of the developer film formed by the developer film forming device. Here, the sensing device 80 detects the concentration of color developer to be measured by using light in a range of wavelengths for which the light transmissivity of the color developer to be measured is low.

The housing 50 is formed so that developer can pass through it. The developer film forming device includes a roller 60 rotatably installed in the housing 50, a driving source 70 for rotating the roller 60, and a developer supply device for supplying developer to the roller 60.

The housing 50 includes a supply portion 53 filled with developer to a predetermined level. Developer flows into the supply portion 53 through a supply pipe 53a. A flow control valve (not shown) is installed in the supply pipe 53a for controlling the amount of the supplied developer so that developer of a predetermined amount can be supplied. The developer supplied through the supply pipe 53a is exhausted back to the container (21 of FIG. 1) through an exhaust pipe 55a provided at the lower portion of the housing 50. Here, the exhaust pipe 55a is preferably large enough to prevent developer from remaining in the housing 50.

The supply portion 53 and the roller 60 are separated by a partition 57 which has a predetermined height from the bottom surface of the housing 50. Thus, when the amount of developer supplied to the supply portion 53 through the supply pipe 53a is sufficient, the developer in the supply portion 53 flows toward the roller 60 along the partition 57.

A wall portion 59 having a predetermined height is provided at least at one side of the supply portion 53, separated from the inner wall of the housing 50. When an excessive amount of developer is supplied to the supply portion 53 from the supply pipe 53a, the excessive developer overflows the wall portion 59 into the space formed between the wall portion 59 and the inner wall of the housing 50. Also, the wall portion 59 is preferably formed to extend up to the side of the roller 60. This is to make the developer supplied to the roller 60 to overflow into the space between the wall portion 59 formed to extend to the side of the roller 60 and the inner wall of the housing 50 such that the roller 60 contacts the developer at a substantially constant height.

Also, a buffer member 58 for reducing the flow rate of developer supplied from the supply pipe 53a is preferably installed in the supply portion 53, protruding from the partition 57. The buffer member 58 can be installed at the wall portion 59 and/or the inner wall of the housing 50. In the present embodiment, the buffer member 58 is formed to be slanted downward to be directed to the supply portion 53. Also, a shielding member 56 is installed at the ceiling of the housing 50 to extend downward therefrom, so that a gap of a predetermined width can be formed between the shielding member 56 and the partition 57. The shielding member 56 is for preventing defective and irregular flow of developer flowing from the relatively narrow supply pipe 53a to the relatively wider supply portion 53 from the supply portion 53 to the roller 60 generated due to malfunction of a pump, and for maintaining the level of developer at one side of the roller 60 constant. Hence, variations in thickness of the developer film formed on the surface of the roller are minimized and the measurement of concentration of the developer becomes accurate.

After the developer film formed on the surface of the roller 60 is detected by the sensing device, a cleaning member such as a blade 90 to clean the rotating roller 60 is installed to be capable of contacting the surface of the roller 60.

One end of the blade 90 is installed at the upper portion of the partition 57 and the front edge thereof contacts the surface of the roller 60. At least one side end of the blade 90 contact the wall portion 59. Thus, the blade 90 serves as a guide member for guiding the developer flowing over the partition 57 and simultaneously forms a space S with the wall portion 59. Preferably, the blade 90 is installed to be inclined to the downside of the roller 60. In this case, the developer supplied from the supply portion 53 flows toward the roller 60 while being guided along the blade 90 and fills the space S to a predetermined height. That is, the developer inputting between the partition 57 and the shielding member 56 is restricted by the blade 90 contacting the surface of the roller 60 so as not to hardly flow toward the downside of the roller 60. Here, the height which one side of the roller 60 is submerged in the developer filling the space S is approximately determined by the height of the gap between the shielding member 56 and the partition 57 and the installation position of the roller 60 with respect to the gap. Here, it is possible that the blade 90 be installed to not contact the roller 60, to perform only the function of guiding member, and an additional member be installed for cleaning.

As the level of developer in the space S increases, the excess developer naturally overflows the wall portion 59. Thus, the level of developer in the space S hardly varies.

In this state, when the roller 60 is rotated counterclockwise by driving the driving source 70, as shown in FIG. 3, a developer film f of a predetermined thickness is formed on the surface of the roller 60. Here, as long as the level of developer in the space S is constant, the thickness of the developer film f can be maintained constant.

Here, the driving source 70 includes a driving motor 71 such as a typical stepping motor capable of constantly driving and a reduction gear assembly 73 which reduces the rotation speed of the driving motor 71 and transfers the reduced rotation force to the roller 60. Thus, by means of the driving source 70, the roller 60 is constantly driven at a low speed.

In the process of forming a developer film with a developer concentration measuring apparatus having the above structure, first, to measure the concentration of the developer supplied to the development unit (20 of FIG. 1), first developer from the container 21 is supplied to the supply portion 53 through the supply pipe 53a. Some of the developer in the supply portion 53 flows toward the roller 60 through the gap between the partition 57 and the shielding member 56. The remaining developer flows over the wall portion 59 to the bottom of the housing 50 and then is exhausted through the exhaust pipe 55a. The developer flowing through the gap fills the space S to a predetermined level by being restricted by the blade 90 in contact with the roller 60. Thus, one side of the roller 60 is submerged in the developer to a predetermined level. Here, when the amount of developer flowing in the space S through the gap increases, the excessive developer flows over the wall portion 59 installed at both sides of the roller 60, onto the bottom of the housing 50 and then is exhausted through the exhaust pipe 55a so that the level of the developer filling the space S is constantly maintained. In this state, when the roller 60 rotates at a predetermined rotational speed driven by the driving source 70, a developer film having a predetermined thickness is formed on the surface of the roller 60. Then, the concentration of the developer film is measured by the sensing device 80.

As the roller 60 continues to rotate, most of the developer film on the surface of the roller 60 drips off onto the bottom of the housing 50 due to gravity, and any developer remaining on the surface of the roller 60 is cleaned off by the blade 90. The developer on the bottom of the housing 50 is exhausted through the exhaust pipe 55a.

Accordingly, when the concentrations of the developers are set between about 2.5–3.5 wt % to appropriately maintain print quality, the rotation linear velocity of the roller 60 is set to 122 rpm, and one side of the roller 60 is submerged in the developer filling space S such that the angle between the center of the roller 60 and the horizontal surface of the developer when settled in the space S corresponds to about 10°–20°, a thin developer film having a thickness of about 50 through 100 $\mu$m can be formed on the surface of the roller 60.

The above description is concerned with a specific preferred embodiment of the present invention insofar as it relates to forming a developer film, and it is obvious that various embodiments are possible.

In the present preferred embodiment, a reflection member 61 is provided on at least part of the surface of the roller 60. In this case, the sensing device 80 is a reflection type and includes a light source unit 81 installed outside the roller 60 for emitting colored light within a predetermined wavelength range to the developer film formed on the reflection member 61, and a main photodetector 83 installed adjacent to the light source unit 81 for receiving the light passing through the developer film f and reflecting from the reflection member 61. Here, the light source unit 81 is preferably installed above the roller 60 to emit light to the developer film formed on the top of the roller 60 where variations in the thickness of the developer film can be minimized in a predetermined area.

A monitoring photodetector 85 for monitoring the optical output of the light source unit 81 by detecting part of the light emitted from the light source unit 81 is installed at one side of the light source unit 81. When the detection signal of the monitoring photodetector 85 is fed back to an apparatus (not shown) driving power the light source unit 81, to adjust driving current of the light source unit 81, the optical output of the light source unit 81 is stabilized. Also, when the detection signal of the main photodetector 83 is corrected by the detection signal of the monitoring photodetector 85, the same results as a case in which a constant flux of light is emitted to the developer film, regardless of the variations in the flux of light emitted from the light source unit 81, can be obtained.

Here, a typical photodiode or a CdS cell can be used as the main and/or monitoring photodetectors 83 and 85.

Preferably, the sensing device 80 further includes a concentration calculation portion (not shown). The concentration calculation portion compares the detection signal of the main photodetector 83 with reference data of a lookup table to determine and output the concentration signal. Preferably, to minimize the effect of external light on the developer concentration measuring apparatus, the housing 50 is formed of an opaque material or the outer surface thereof is processed to black.

The light transmissivity of color developers such as yellow, magenta and cyan typically differs according to the range of wavelengths of the irradiated light and for each color of developer, there is a range of wavelengths for which the transmissivity of the color developer is approximately equivalent to the light transmissivity of black developer.

Thus, the light source unit 81 according to the present invention is characterized in that the concentration of a selected color developer is measured by emitting colored light corresponding to the range of wavelengths for which the developer has a relatively lower light transmissivity, in particular, the light transmissivity of black developer.

In particular, when the selected color developers are yellow, magenta and cyan developers, the emitted light wavelengths correspond to blue, green and red colored light, respectively.

According to the present invention, the ranges of wavelengths used as blue, green and red light are preferably about 400–470 nm, 500–580 nm and 630–700 nm, respectively, and the optimal values therefor are about 436 nm, 546 nm and 700 nm, respectivley. Also, the broadest ranges of wavelengths used for blue, green and red light are about 370–500 nm, 460–610 nm and 550–780 nm, respectively.

When light in the range of wavelengths for which the developer has a lower light transmissivity is emitted, the light transmissivity of the selected color developer decreases as low as the light transmisivity of black developer. Thus, when the selected color developer is contaminated by black toner, the overall light transmissivity is not much affected. Also, as the developer film is thin, the colored light can pass through even when the developer is contaminated by a small amount of black toner. Thus, the concentration of the selected color developer can be detected close to the actual concentration without a considerable error when there is contamination by a small amount of black toner.

In the case of contamination by a small amount of another color toner, because a color toners exhibit excellent light transmissivity with respect to the colored light, the contamination does not much affect the measurement of the concentration of the selected color developer.

Figure 4:
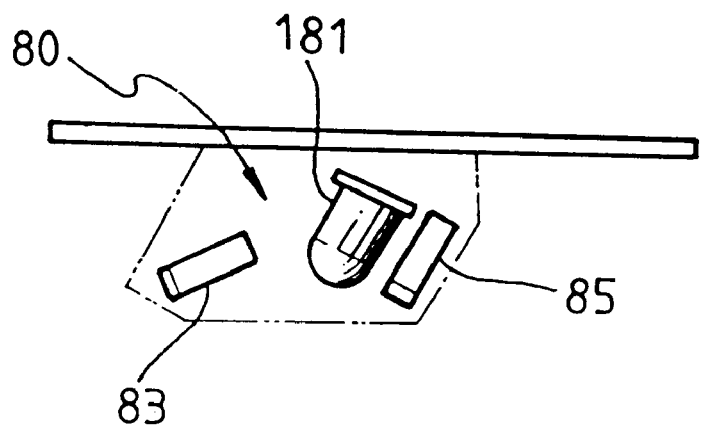
FIGS. 4 through 6 are views of preferred embodiments of a light source unit of FIG. 2.

To emit colored light corresponding to the selected color developer to the developer film, a light emitting diode 181 emitting blue, green and red light in the above-described wavelength range can be used as the light source unit 81 according to the present invention, as shown in FIG. 4.

Figure 5:
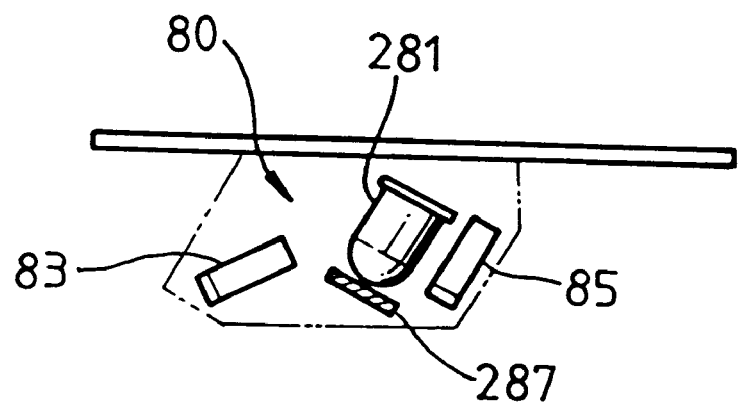

Also, the light source unit 81, as shown in FIG. 5, may include a white light source 281 and a filter 287 for passing blue, green or red light in the above-described wavelength range among the light emitted from the white light source 281. Here, a light emitting diode emitting white light or a halogen lamp is used as the white light source 281.

Figure 1:
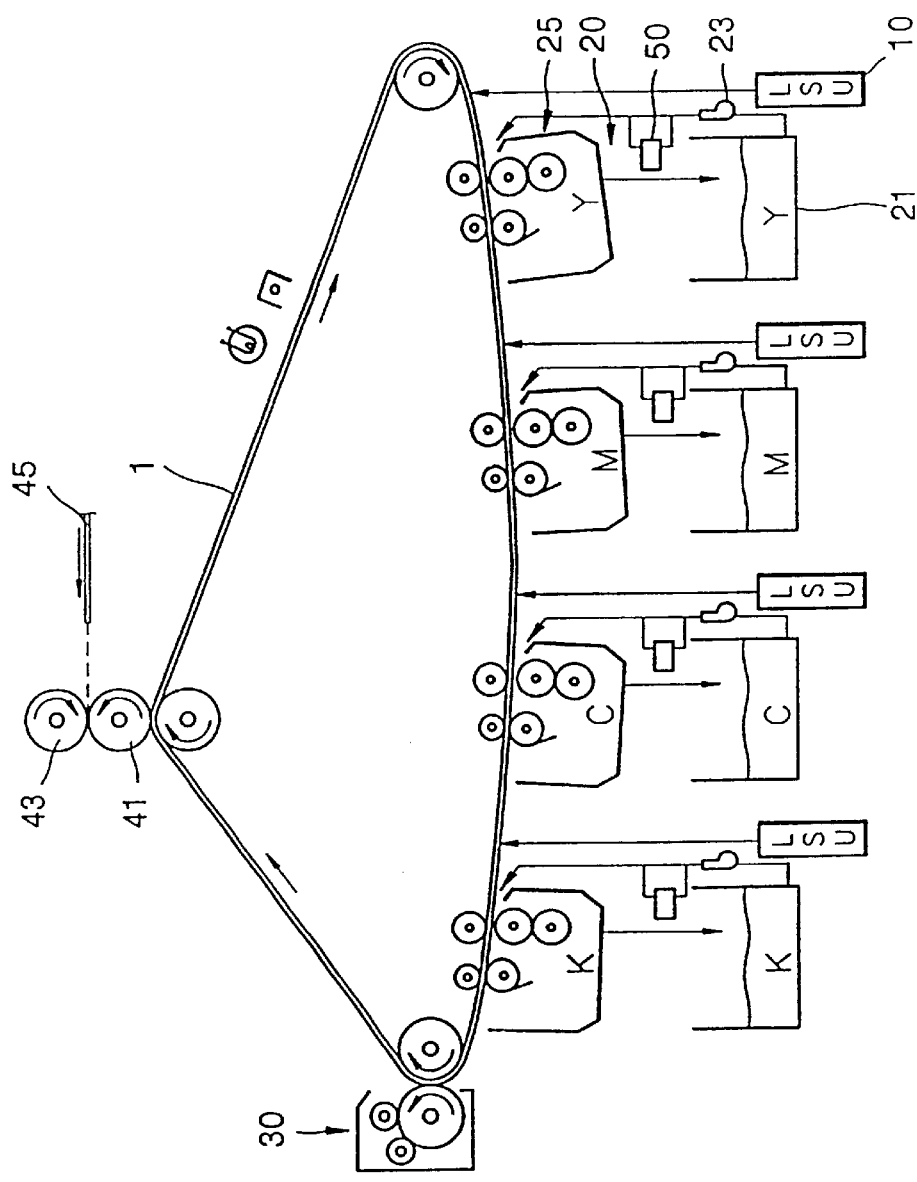
FIG. 1 is a view showing the structure of a conventional liquid electrophotographic color printer.
Figure 6:
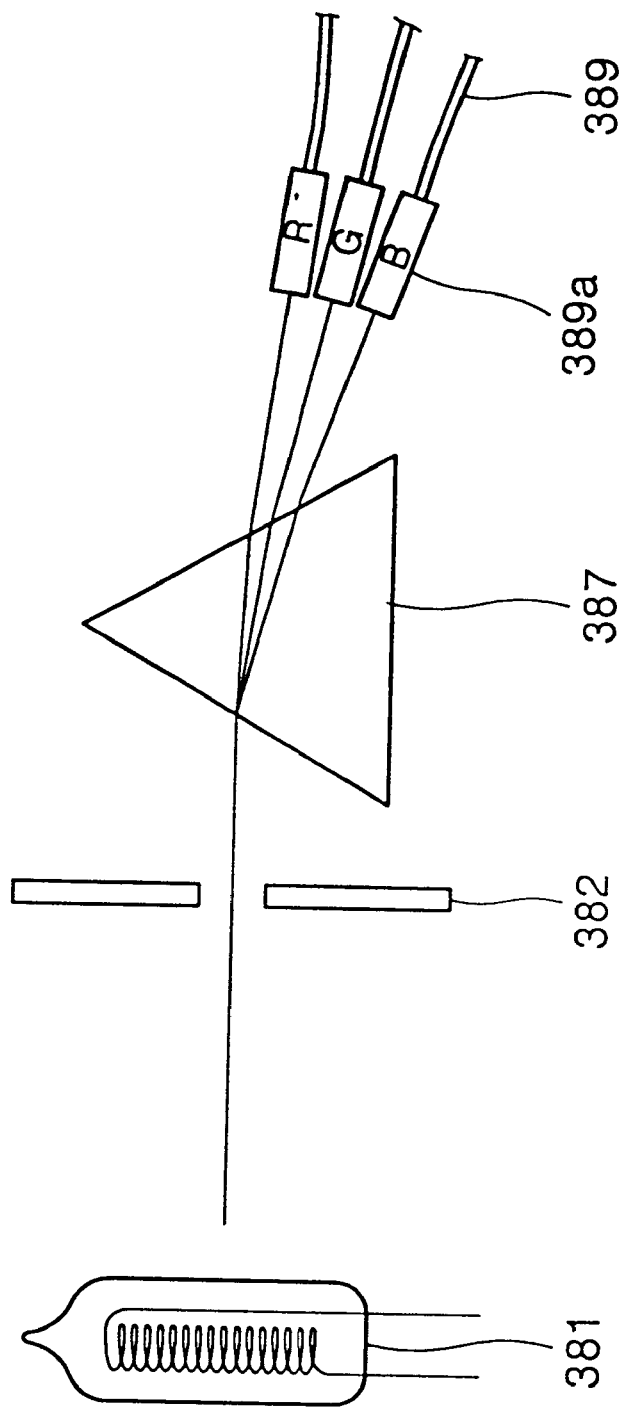

Also, the light source unit 81, as shown in FIG. 6, may include a white light source 381 and a spectrum member such as a prism 387 or grating for splitting the light emitted from the white light source 381 according to the wavelength thereof. Here, an optical cable 389 is preferably provided to transmit blue, green or red light in the above-described wavelength range of the light split by the spectrum member, to be emitted to the developer film. An input portion 389*a* of the optical cable 389 is installed near the spectrum member and receives the colored light, and the output portion thereof (not shown) is installed near the roller 60 to emit the light toward the developer film. It is advantageous that the light source unit can be used as a common light source for a plurality of developer concentration measuring apparatuses in a color printer as shown in FIG. 1. Here, the colored light corresponding to each color developer is transmitted to the appropriate concentration measuring apparatus using the optical cables 389. Here, reference numeral 382 denotes a slit member.

The light source units of FIGS. 4 and 6 may include the filter (287 of FIG. 5) for emitting light of the appropriate color having a narrower wavelength range to the developer film.

Figure 7:
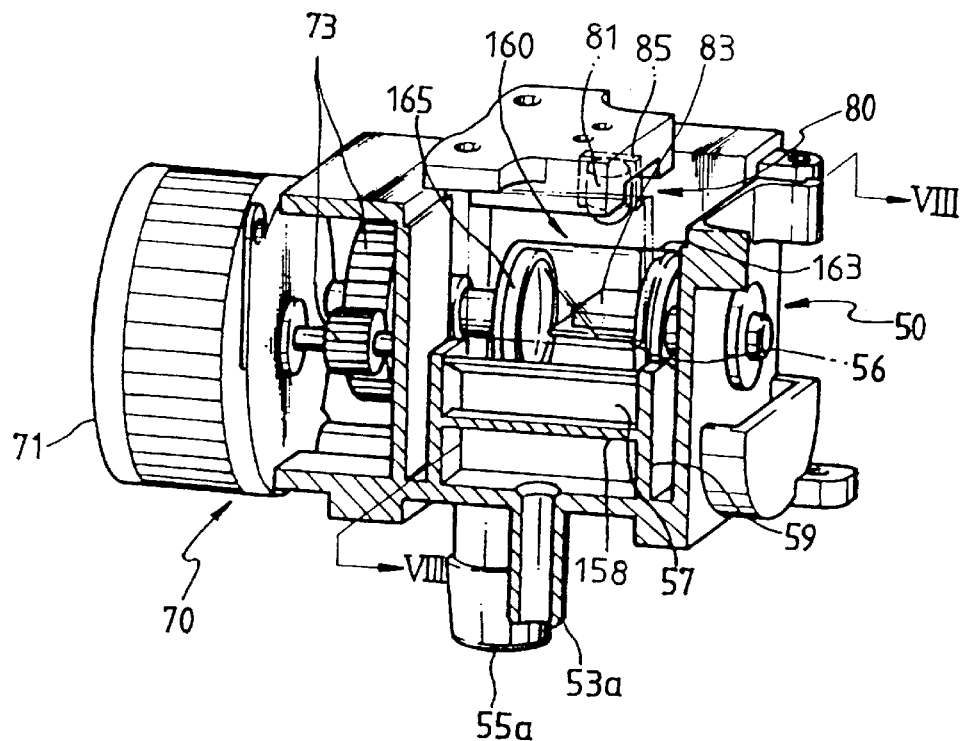
FIG. 7 is a partially cut-away perspective view showing an apparatus for measuring the concentration of developer in a liquid printer according to another preferred embodiment of the present invention.
Figure 8:
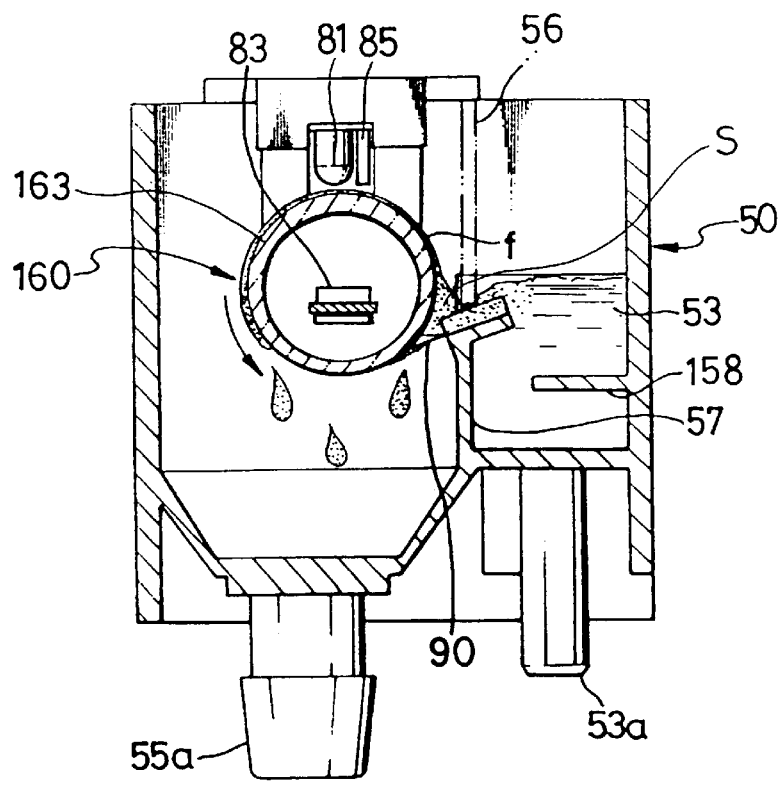
FIG. 8 is a sectional view taken along the line VIII—VIII of FIG. 7.

FIG. 7 shows an apparatus for measuring the concentration of developer in a liquid printer according to another preferred embodiment of the present invention. FIG. 8 is a front side sectional view of FIG. 7. The same reference numerals as those used in FIGS. 2 and 3 denote the same members having the same functions.

The present preferred embodiment concerns an apparatus for measuring the concentration of developer having a transmission type sensing device, unlike the above preferred embodiment. At least part of a roller 160 is formed of a transparent member 163. That is, the roller 160 includes a body 163 formed of a transparent pipe such as a glass pipe and a flange 165 installed at both sides of the body 163.

The light source unit 81 and the main photodetector 83 which are structural elements of the sensing device according to the present embodiment are installed one inside and one outside the roller 160 to face each other. For example, the light source 81 can be installed outside the roller 160 and the main photodetector 83 can be installed inside the roller 160, or the light source 81 can be installed inside the roller 160 and the main photodetector 83 can be installed outside the roller 160. Thus, the light emitted from the light source unit 81 passes through the developer film formed on the surface of the roller 160 and the transparent member 163 and is received by the photodetector 83 disposed to face the light source 81. Here, it is preferred that the light source 81 and the photodetector 83 are arranged to be roughly perpendicular to the surface of the roller 160 so that light can be transmitted perpendicularly through the developer film. Reference numeral 158 denotes a buffer member installed to protrude from the inner wall of the housing 50.

Here, any of the light sources previously described with reference to FIGS. 4 through 6 can be used as the light source unit 81. When the light source unit of FIG. 6 is used, preferably, an output end (not shown) of the optical cable 389 is arranged outside the roller 160 and the main photodetector 83 is disposed inside the roller 160.

The principle of measuring the concentration of developer close to the actual concentration by the developer concentration measuring apparatus according to the present invention, when the developer is contaminated, will be described by taking yellow developer as an example.

As a yellow toner is dispersed in yellow developer, when a developer film of about 50–100 $\mu$m thick is formed on the roller 60 or the roller 160, the yellow toner does not completely cover the surface of the rollers. Therefore, when blue light in a range of wavelengths above-described is emitted to the yellow developer film, although the yellow toner absorbs part of the light, some light passes between toner particles and a predetermined light transmissivity exists.

Even when the yellow developer is contaminated by a black toner, as the degree of contamination allowed in a printer is very small, concentration of the black toner is much lower than that of the yellow toner. Also, the light transmissivity of the black toner with respect to the blue light is low. Thus, it is nearly impossible discern the black toner and the yellow toner in concerned blue light. Thus, when the concentration of yellow developer is measured by the apparatus according to the present invention, as contamination by a black toner does not much affect the determination of the concentration of the yellow developer, the measured value is very close to the actual concentration and quite reliable.

When the yellow developer is contaminated by magenta and cyan toner, because the light transmissivity of magenta and cyan toner is about 60% or more with respect to blue light and because the degree of contamination allowed in a printer is very low, the light transmissivity is the same as the case in which magenta and cyan toner do not exist so that the measured concentration value is not affected much.

Here, in the case of magenta and cyan developers, the concentration thereof is measured by emitting green and red light in the above-described wavelength range, respectively. As the principle is substantially the same as the case of the yellow developer, a description thereof will be omitted.

Therefore, the apparatus for measuring the concentration of developer according to the present invention can measure the concentration very close to the actual concentration value regardless of contamination by a toner of another color.

Although the light transmissivity of black toner is low throughout the range of wavelengths including the visible and infrared regions, the black developer has a predetermined light transmissivity when spread out into a thin developer film, so it is possible to measure the concentration of the black developer by the present apparatus. Contamination by a toner of another color does not substantially affect the concentration value of the black developer in a range of a degree of contamination allowed for a printer.

As described above, in the apparatus for measuring the concentration of developer according to the present invention, as a thin developer film is formed and the concentration of developer is measured by emitting colored light in a range of wavelengths for which the transmissivity of the toner is low, the affect of different colored contaminants is less and the concentration of developer can be measured close to the actual concentration although the developer is contaminated.

Thus, as a correction device for correcting errors in the measured concentrations of the contaminated developers is not needed, the structure of the apparatus is simplified and the reliability of the apparatus is high.

What is claimed is:

1. An apparatus for measuring a concentration of developer in a liquid printer, the apparatus comprising:

a housing;

a developer film forming device for forming a developer film, said device installed in the housing; and a sensing device, wherein said sensing device further includes:

a light source unit for emitting a colored light corresponding to a range of wavelengths for which a light transmissivity is relatively low to a developer film formed by a selected color developer, and a photodetector installed corresponding to the light source unit and receiving the colored light emitted by the light source unit and transmitted through the developer film.

2. The apparatus as claimed in claim 1, wherein the selected color developer is yellow, magenta or cyan, and the colored light is blue, green or red light, said blue, green or red light corresponding to said yellow, magenta and cyan developer, respectively.

3. The apparatus as claimed in claim 2, wherein the blue, green and red light have wavelength ranges of about 400–470 nm, 500–580 nm and 630–700 nm, respectively.

4. The apparatus as claimed in claim 3, wherein the blue, green and red light have wavelength of about 436 nm, 546 nm and 700 nm, respectively.

5. The apparatus as claimed in claim 1, wherein the light source unit is a light emitting diode emitting one of a blue, green and red light.

6. The apparatus as claimed in claim 1, wherein the light source unit comprises a white light source and a filter, wherein said filter is intended for passing blue, green or red light of the light emitted from the white light source.

7. The apparatus as claimed in claim 1, wherein the light source unit comprises:

a white light source;

a spectrum member for splitting a light emitted from the white light source according to wavelengths of the light; and at least one optical cable through which a light produced after spitting is guided to the developer film, wherein the light produced after splitting is of a predetermined wavelength for which the light transmissivity of a selected color developer is relatively low.

8. The apparatus as claimed in claim 1, wherein the developer film forming device comprises:

a roller rotatably installed in the housing;

a driving source for rotating the roller; and a developer supply device for supplying developer to the roller so that a developer film can be formed according to a rotation of the roller.

9. The apparatus as claimed in claim 8, wherein a reflection member is provided on at least a part of a surface of the roller, and the light source unit and the photodetector are installed outside the roller to correspond to each other.

10. The apparatus as claimed in claim 8, wherein at least a part of the roller is formed of a transparent member, and the light source unit and the photodetector are installed inside and outside the roller, respectively, such that they are facing each other through the transparent member.

11. The apparatus as claimed in claim 8, wherein the developer supply device comprises:

a supply portion filled with developer;

a partition installed in the housing for sectioning the supply portion and the roller; and a guide member having one end thereof coupled to the partition and the other end thereof installed close to a surface of the roller, for guiding developer overflowing the partition toward the roller, wherein at least a part of the roller can be submerged to a predetermined position in the developer supplied from the supply portion.

12. The apparatus as claimed in claim 11, wherein the guide member is installed to be capable of contacting the surface of the roller to clean the surface of the roller.

13. The apparatus as claimed in claim 11, further comprising a wall portion contacting both sides of the guide member and installed to be separated from a side wall of the housing, so that a space is formed at one side of the roller by the guide member and the wall portion.

14. The apparatus as claimed in claim 11, further comprising:

a supply pipe installed at a lower portion of the supply portion for allowing the developer to flow into the housing;

a buffer member installed in the supply portion for buffering the flow of developer supplied from the supply pipe; and a shielding member installed in the housing forming a gap with the partition, for blocking an irregular flow of developer flowing from the supply portion toward the roller.

15. The apparatus as claimed in claim 8, wherein at least a part of the roller is formed of a transparent member, and the photodetector and the light source unit are installed inside and outside the roller, respectively, such that they are facing each other through the transparent member.

* * * * *